Sept. 10, 1968 Q. MANSUINO Plant Pat. 2,833
ROSE PLANT
Filed March 1, 1967
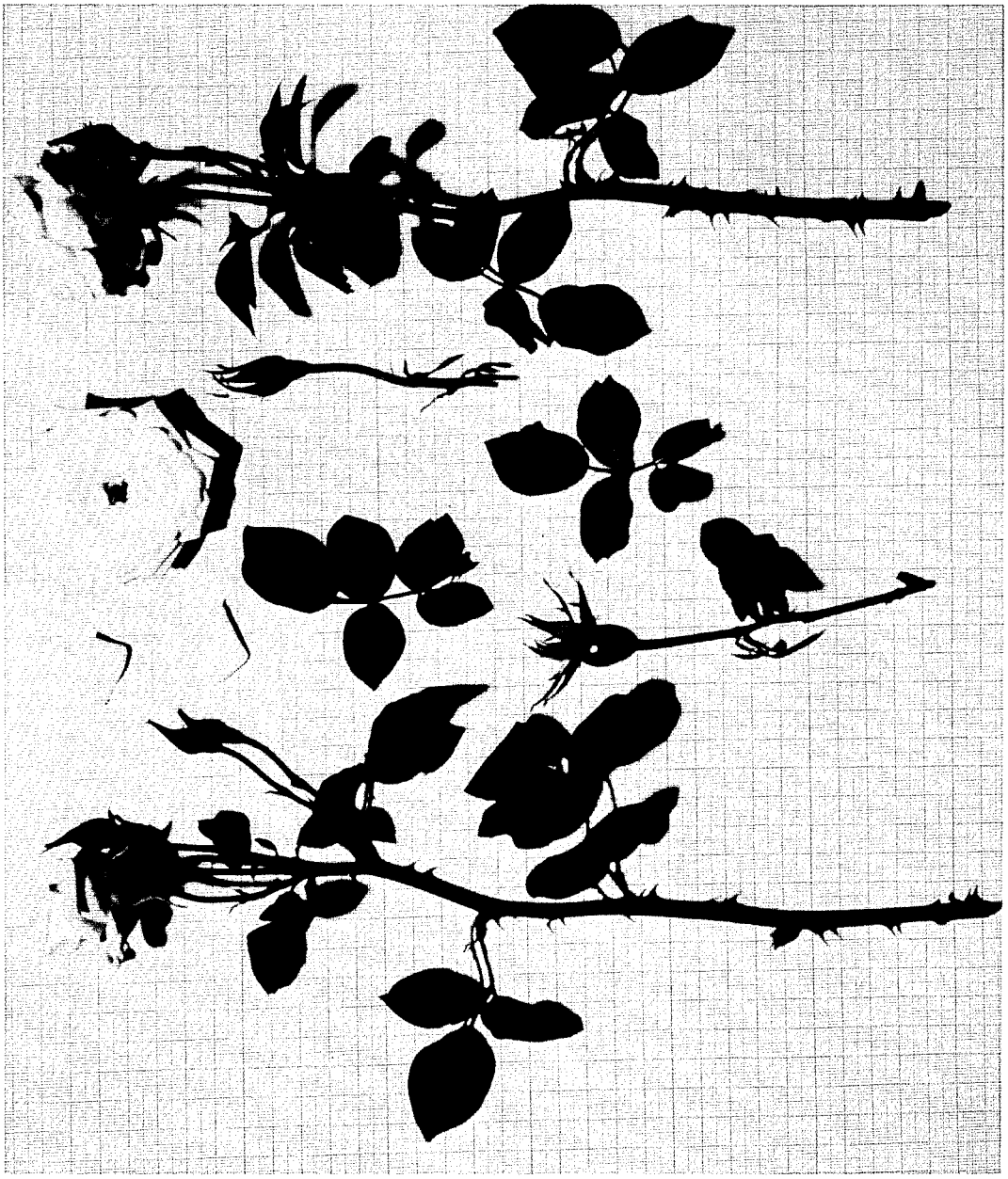
Inventor.
Quinto Mansuino
By: Robb & Robb
Attorneys.

United States Patent Office

Plant Pat. 2,833
Patented Sept. 10, 1968

2,833
ROSE PLANT

Quinto Mansuino, San Remo, Italy, assignor to Carlton Rose Nurseries, Inc., Carlton, Oreg., a corporation of Oregon

Filed Mar. 1, 1967, Ser. No. 619,878
Claims priority, application Italy, Sept. 7, 1966, 20,410/66
1 Claim. (Cl. Plt.—23)

The present invention relates to a new and distinct variety of rose plant of a class falling between the dwarf and the hybrid tea types, which was originated by me in the course of an extended breeding program culminating in the crossing of two unnamed and unpatented white-flowered varieties identified in my breeding records as *Rosa mansuiniana* #2035 and *Rosa mansuiniana* #P.N. 65, the former being the seed parent and the latter being the pollen parent.

As the result of this breeding, I have produced a new and improved variety which fulfills a long need in the cut flower trade, and which is distinguished from its parents, as well as from all other varieties of which I am aware, as evidenced by the following unique combination of characteristics which are outstanding in the new variety:

(1) A vigorous habit of growth which is unaffected in different types of soil;

(2) Good flower productivity suitable for commercial culture;

(3) A smaller flower size than those usually cultivated for commercial cut flowers;

(4) Lighter and particularly elegant flowers which, even in their reduced size, are of harmonious proportions; and (5) A substantially pure white flower color.

Asexual reproduction of my new variety by grafting and budding, as performed by me at San Remo, Italy, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in an illustration of this character.

The following is a detailed description of my new variety, with color terminology in accordance with Robert F. Wilson's Horticultural Colour Chart, except where general color terms of ordinary dictionary significance are obvious:

Parentage: Seedling.

*Seed parent.*—An unnamed seedling identified as *Rosa mansuiniana* #2035.

*Pollen parent.*—An unnamed seedling identified as *Rosa mansuiniana* #P.N. 65.

Classification: Between dwarf and tea.

*Plant*

(Observations made from specimens grown both outdoors and in greenhouses at San Remo, Italy, during the month of May.)

Growing habit: Bushy; strong; compact; upright; spreading; with branches and floral stems little or moderately divergent from the axis of the plant; floral stems from moderately numerous to numerous.

Average height: From about 4⅔ feet to 5⅓ feet for plants two years old and fully developed.

Stalk: Variable in size and shape, but ranging about 10 inches to 1 foot long and from about 7/16 inch to 11/32 inch in diameter; cylindrical; straight or slightly sinuous.

Main branches: Relatively few; average from 2 to 4 starting from the grafting point or from the base of other branches; upright; ascendent; straight; slightly diverging from each other.

*Shape.*—Almost cylindrical; articulated in numerous short to medium long internodes of an average length of 1⅜ inches to 1¾ inches; nodes differentiated, with a few prominent on the branches.

*Size.*—Variable according to the cutting system employed in the culture; average length from 1⅓ to 2⅓ feet; average diameter at the base from 7/16 inch to 11/32 inch.

*Bark.*—From moderately thick to thick; smooth; slightly satiny; pruinose or opaque on some parts.

*Thorns.*—From moderately numerous to numerous; average number of 4 to 8 per internode; slightly variable in size, with a few prickles of medium size among the thorns; triangular shape; thin and elongated; easily detachable from the bark; long and acutely pointed, with point slightly bent downward; base oval and slightly larger in the upper portion; average length of thorns from ¼ inch to 5/16 inch; average breadth from 1/16 inch to ½ inch; average thickness from ⅛ inch to 3/16 inch. Color—Satiny Hazelnut Brown. Texture—spongy; hard; resistant.

Floral stems: Numerous, starting from the upper nodes of the branches at intervals of from 1⅜ inches to 1¾ inches long; average number from 4 to 8 on each primary branch in different stages of development; moderately divergent from the axis of the plant.

*Shape.*—Almost cylindrical; slightly decreasing in diameter from the base to the apex; from straight to slightly sinuous; sometimes slightly angulated on the nodes; thin and elongated; from about 1⅓ feet to 2⅓ feet long; nodes slightly differentiated and slightly prominent on the stems.

*Size.*—Average length from 1⅓ feet to 2⅓ feet; average diameter at base from 5/32 inch to ¼ inch.

*Bark.*—Moderately thick; smooth; glabrous; satiny or opaque.

*Color.*—Between Spinach Green, page 187, tones 60 to 60/1–2–3 and Parsley Green, page 193, tones 62/2–3.

*Thorns.*—Moderately numerous; slightly more numerous at the base of the stems; average number of 4 to 6 on each internode; slightly variable in shape but generally triangular; elongated with an acute differentiated point; slightly hooked downward; base oval-rounded; average length from ¼ inch to 9/16 inch; average breadth from 3/16 inch to ⅝ inch; average thickness from 3/32 inch to ¼ inch. Color—Lettuce Green, page 176, tones 61/2–3. Texture—moderately tender; easily detachable from the bark.

Leaves: Abundant; from medium size to large; inserted singly on each node; spread on the stems and on the branches.

*Shape.*—Long and narrow; compound of 3–5 or sometimes 7 leaflets; inserted on opposite pairs, with a terminal leaflet on a thin and elongated rachis.

*Size.*—Variable with the position on the stem; decreasing from the lower to the upper part of the plant; average length from the base of the rachis to the point of the terminal leaflet from 4 inches to 6 inches; average breadth between the external points of the opposite leaflets from 2¾ inches to 3½ inches.

*Leaflets.*—Rounded-oval; acutely pointed and semicircular at the base; limb flat; edges finely dentate;

teeth from small to medium size. Growing habit—leaflets flat on the leaf plane; diverging from the rachis at angles of about 90°. Size—variable with position on the rachis; increasing from the basal pair to the terminal leaflet as follows: First pair on the base, average length from ¾ inch to 1 inch, average breadth from 7/16 inch to ⅝ inch; second pair from the base, average length from 1 inch to 1 3/16 inches, average breadth from ⅝ inch to 1 inch; third pair from the base, average length from 1 7/16 inches to 1¾ inches, average breadth from ⅞ inch to 1 3/16 inches; terminal leaflet, average length from 1 7/16 to 1¾ inches, average breadth from 1 inch to 1 7/16 inches. Surface: upper side—smooth; glabrous; medium glossy; with pennate veins hollowed in the limb; under side—smooth; glabrous; opaque; with pennate veins prominent on the limb. Color: upper side—Ivy Green, page 200, tones 60/2–3; under side—near Lavender Green, page 196, tones 61–61/1. Texture—thin; resistant. Rachis—thin; semi-cylindrical, with a longitudinal hollow of moderate depth; with glandular hairs on the edges; some thin, elongated, hooked and moderately resistant thorns in an average number of 3 to 5 on the underside of the rachis. Stipules—very differentiated; finely hairy and dentate on the edges; adnate to the base of the rachis until about the half of the basal internode, ending in triangular points from 3/16 inch to 5/16 inch long; divergent from the rachis at angles of from 45° to 50°.

Lateral sprouts: Inserted on many of the upper nodes of the stems in different stages of development; from 2 to 4 upper nodes each bearing a lateral sprout articulating from 1 to 3 internodes, supporting a small secondary floral bud; at the base of the floral peduncle there are often present 2 other lateral peduncles with small secondary floral buds.

Floral peduncle: Upright; cylindrical; thin; flexible; bearing small, moderately numerous glandular hairs. Color—Spinach Green, page 187, tone 60/1.

*Flowers*

Growing habit: From small to medium size; inserted terminally and singly on the floral stems, accompanied by 2 to 4 small secondary floral buds which open after the principal flowers; this growing habit partly relates this rose to the type of inflorescence in clusters, but this variety has a main flower singly borne on the stem and more developed than the others.

Floral bud: Ovoid; much elongated; with a cone-shaped receptacle and much elongated sepals; sometimes turbinated; surmounted by foliaceous appendages at the point and bearing thin lanceolated appendages inserted on the edges of the sepals and divergent from them and from the floral bud. Size—average length from 1 inch to 1 3/16 inches; average diameter from 5/16 to 7/16.

Calyx: Compound, with 5 sepals opening like a star under the corolla when it is open; bent downward; inserted on a funnel-shaped receptacle; persistent after the blooming.

*Sepals.*—Limb triangular; much elongated and slightly lanceolated; slightly concave on its internal side, especially near the point; edges of the sepals slightly glandular and tomentose; smooth; almost always bearing some slightly lanceolate appendages, finely indented, and divergent from the edges of the sepals; length of appendages from ¼ inch to 13/32 inch; width of appendages from 1/32 to 1/16 inch. Size—average length from 1⅛ inches to 1 3/16 inches; average breadth at the base from ⅛ inch to 3/16 inch; average width from 5/16 to 13/32 inch. Color: upper surface—Sage Green, page 198, tones 61/2–3, covered by a fine, wooly, white tomentum; under surface—Spinach Green, page 187, tone 60/3. Surface: external face—smooth; glabrous; partially satiny; slightly glandulous; sometimes opaque; internal face—opaque; glandular; covered by a fine and short, wooly tomentum. Texture—medium thickness; rigid; coriaceous.

Half open bud: From ovoid and moderately globous, but becoming cup-shaped, conic or bell-shaped as the flower opens; external petals open slightly separately from the central petals, with slightly rounded edges making moderately acute points at the junction of the rolls; petals arranged regularly in the corolla and being imbricated or slightly turbinated; sepals adherent to the petals or slightly curved downward at this stage of the bloom.

*Size.*—Average length from 1⅛ inches to 1⅜ inches; average diameter from ¾ inch to 1 inch.

*Color.*—Pure white, with green tints at the base of the petals.

Open Corolla: From small to medium size; cup shaped; with petals in separated verticils until almost flat when the opening is finished; outline round or star shaped, with points on the outer edge of the petals at the junction points of the rolls; edges of inner petals less rolled than the outer petals; central petals cup shaped and concaved at their center, and slightly or moderately rolled on the outer edges; some rudimentary petals in the center of the flower; concave at center of the flower making the stamens and pistils visible; profile of the flower ranges from cup-shaped to flat.

*Size when fully open.*—From 2⅜ to 3 3/16 in diameter; length of flower from the receptacle to the apex of the petals from ¾ inch to 1 inch.

*General color.*—Pure white, with light tones of yellowish green at the base of the petals.

*Petals.*—Moderately numerous; average number from 35 to 45; variable in size and shape according to the position in the flower. Outer petals—outline rounded; concave in the center; rolled on the outer edges and moderately convergent toward the base; sometimes slightly wrinkled on the latter edges; outline of the petals on the whole is slightly polygonal, with a moderately acute and differentiated terminal point; attachment of the petals very slightly differentiated. Color—Chartreuse Green, page 90, tones 62/2–3, shading in the white color of the petals. Intermediate petals—similar to outer petals, but more elongated, oval and lanceolated, and less rolled on the outer edges. Central petals—almost triangular, with outer edge rounded and almost spathulate; lateral edges very convergent with the attachment. Size: outer petals—average length from 1 inch to 1⅜ inches; average breadth from 1 inch to 1⅜ inches. Intermediate petals—average length from 1 inch to 1 3/16 inches; average breadth from 13/16 inch to 1 inch; central petals—average length from 15/16 inch to 1 inch; average breadth from ½ inch to 13/16 inch. Color: upper side—pure white, with tones of Chartreuse Green, page 90, tones 62/2–3 at the attachment; under side—same as upper side, with attachment having a small spot shaded with Chartreuse Green, page 90, tones 62/2–3. Surface: upper face—slightly satiny or granulose, with radial veins hollowed in the limb; under face—same as upper face with radial veins prominent on the limb. Texture—thin; tender; velvety.

*Reproductive organs*

Stamens: Average number of 60 to 80 inserted on the outer edge of the receptacle around the styles.

Filaments: Upright; free; moderately thick; variable in length from ⅜ inch to 13/16 inch. Color—Chartreuse Green, page 90, tone 62/3.

Anthers: Large size, biloculated; lance shaped. Color—yellow.

Styles: Average number from 60 to 80 in the center of the receptacle; very thin; narrowed at the base; more free at the ends; contorted. Color—greenish white, surrounded by a thick, short, wooly tomentum at the base.

Stigmas: Funnel shaped; slightly differentiated. Color—yellow.

Scent: Light. Nature—tea.

Blooming habit: Abundant; free.

Disease resistance: Both plant and flowers have very good resistance to ordinary rose diseases, as determined by comparison with other varieties grown under the same conditions at San Remo, Italy.

Weather resistance: Very good resistance to bad weather, as determined in the same manner as disease resistance.

Shipping quality of the flowers: Very good.

Lasting quality of cut flowers: Very long.

I claim:

1. A new and distinct variety of rose plant, substantially as herein shown and described, characterized particularly as to novelty by the unique combination of a vigorous, strong, quick-growing, medium tall plant habit, with medium numerous main branches and floral stems and bearing foliage of medium to large size and harmonizing in color with the color of the flowers, good flower productivtiy especially suitable for the commercial production of cut flowers, with the flowers and floral stems being somewhat smaller in size than those of hybrid tea roses that are normally grown for cut flower production but being of harmonious proportion to the remainder of the plant and varying from small to medium size, said flowers having an attractive cup-shaped form but being open or flat at the termination of the bloom, with the outer edges of the flower petals moderately rolled outward and forming moderately acute points about the outline of the corolla, and the flowers being substantially pure white in color but having Chartreuse Green tints at their center, and said flowers having good resistance to adverse weather and good shipping qualities, as well as having long lasting qualities as cut flowers, and being suitable for cultivation both outdoors and in greenhouses for both ornamental purposes and for cut flower production.

No references cited.

ROBERT E. BAGWILL, *Primary Examiner.*